US012778389B2

(12) United States Patent
Iijima

(10) Patent No.: US 12,778,389 B2
(45) Date of Patent: Nov. 3, 2026

(54) ENDOSCOPE CIRCUIT BOARD, ENDOSCOPE AND ENDOSCOPE POWER RECEIVING METHOD

(71) Applicant: OLYMPUS MEDICAL SYSTEMS CORP., Tokyo (JP)

(72) Inventor: Taiga Iijima, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 152 days.

(21) Appl. No.: 18/661,947

(22) Filed: May 13, 2024

(65) Prior Publication Data

US 2024/0382072 A1 Nov. 21, 2024

Related U.S. Application Data

(60) Provisional application No. 63/467,671, filed on May 19, 2023.

(51) Int. Cl.
*A61B 1/00* (2006.01)
*A61B 1/04* (2006.01)

(52) U.S. Cl.
CPC ...... *A61B 1/00114* (2013.01); *A61B 1/00006* (2013.01); *A61B 1/00018* (2013.01); *A61B 1/00027* (2013.01); *A61B 1/00124* (2013.01); *A61B 1/00128* (2013.01); *A61B 1/041* (2013.01); *A61B 1/00119* (2013.01)

(58) Field of Classification Search
CPC ............ A61B 1/00114; A61B 1/00006; A61B 1/00018; A61B 1/00027; A61B 1/00124; A61B 1/00128; A61B 1/041; A61B 1/00119
See application file for complete search history.

(56) References Cited

U.S. PATENT DOCUMENTS

2016/0249908 A1* 9/2016 Shelton, IV .............. H02J 7/00 227/175.1
2019/0117053 A1* 4/2019 Ogihara ............. G02B 23/2469
2020/0026059 A1* 1/2020 Tachikawa ............. H04N 23/66

FOREIGN PATENT DOCUMENTS

JP 5963990 B2 8/2016

* cited by examiner

*Primary Examiner* — Nasim N Nirjhar
(74) *Attorney, Agent, or Firm* — Scully, Scott, Murphy & Presser, P.C.

(57) ABSTRACT

An endoscope circuit board includes: a first power supply system; a second power supply system; a first switch; and a voltage detection circuit, in which when the first switch receives a signal from the voltage detection circuit, if only the first power receiving section receives power, the power received by the first power receiving section is supplied to the first power supply circuit and the second power supply circuit and when the first power receiving section and the second power receiving section receive power, the power received by the first power receiving section is supplied to the first power supply circuit and the power received by the second power receiving section is supplied to the second power supply circuit.

12 Claims, 12 Drawing Sheets

FIG. 8

| FIRST POWER RECEIVING SECTION | SECOND POWER RECEIVING SECTION | OUTPUT OF VOLTAGE DETECTION CIRCUIT | NUMBER OF POWER SUPPLY SYSTEMS |
|---|---|---|---|
| L | L | L | 3 |
| L | H | L | 3 |
| H | L | H | 1 |
| H | H | L | 3 |

ENDOSCOPE CIRCUIT BOARD, ENDOSCOPE AND ENDOSCOPE POWER RECEIVING METHOD

RELATED APPLICATION DATA

This application is based on and claims priority under 35 U.S.C. § 119 to U.S. Provisional Application No. 63/467,671, filed on May 19, 2023, the entire contents of which are incorporated herein by reference.

TECHNICAL FIELD

The disclosure relates to an endoscope circuit board, an endoscope and an endoscope power receiving method.

BACKGROUND

Conventionally, endoscope systems have been widely used for medical or industrial applications. Each endoscope system in general is equipped with an endoscope, a video processor and a monitor, configured to process images picked up by the endoscope using the video processor and display the images on the monitor. In operating such endoscope systems, users may replace some apparatuses with apparatuses of a newer generation relative to the apparatuses (so-called new apparatuses). For example, the user may replace an old video processor with a new video processor.

Japanese Patent Publication No. 5963990 discloses an endoscope system configured to eliminate an image processing setup burden on a user for replacement when the user replaces an old video processor with a new video processor and allow the user to observe images with similar hues before and after the replacement.

SUMMARY

An endoscope circuit board according to an aspect of the disclosure includes: a first power supply system, the first power supply system comprising: a first power receiving section, a first power supply circuit, and a first electric wire connecting the first power receiving section and the first power supply circuit; a second power supply system, the second power supply system comprising: a second power receiving section, a second electric wire connected to the second power receiving section, a second power supply circuit, and a third electric wire; a first switch, the first switch being connected to the third electric wire to switch between a first state in which the second electric wire and the third electric wire are electrically connected and a second state in which the first electric wire and the third electric wire are electrically connected; and a voltage detection circuit configured to: send a signal to the first switch only when power is supplied from the first power receiving section without any power being supplied from the second power receiving section; wherein when the first switch receives a signal from the voltage detection circuit, if only the first power receiving section receives power by causing the first electric wire and the third electric wire to connect, the power received by the first power receiving section is supplied to the first power supply circuit and the second power supply circuit, and when each of the first power receiving section and the second power receiving section receive power, the power received by the first power receiving section is supplied to the first power supply circuit and the power received the second power receiving section is supplied to the second power supply circuit.

An endoscope according to another aspect of the disclosure includes the above-described endoscope circuit board.

An endoscope power receiving method according to a further aspect of the disclosure includes: when an endoscope is connected to an endoscope processor of a first type having only a first power supply, receiving power at a first power receiving section of the endoscope from the first power supply; and electricity connecting from the first power receiving section to a first power supply circuit and a second power supply circuit of the endoscope; and when the endoscope is connected to an endoscope processor of a second type having the first power supply and a second power supply; receiving power at the first power receiving section of the endoscope from the first power supply; electricity connecting from the first power receiving section to the first power supply circuit of the endoscope; supplying power from the second power supply to a second power receiving section of the endoscope; and electricity connecting from the second power receiving section to the second power supply circuit of the endoscope.

BRIEF DESCRIPTION OF THE DRAWINGS

FIG. 8 is a diagram illustrating a truth table of the voltage detection circuit;

DETAILED DESCRIPTION

Generally, when an old video processor is replaced with a new video processor, an endoscope compatible with the old video processor needs to be replaced with an endoscope compatible with the new video processor, which may result in increased cost. Therefore, an endoscope compatible with both the old and new video processors may be required.

The old video processor and the new video processor may have different numbers of power supply system. For example, there may be a case where the old video processor has three power supply systems, whereas the new video processor has one power supply system. Therefore, an endoscope compatible with video processors with different numbers of power supply system may be required.

According to an embodiment described below, it is possible to provide an endoscope circuit board, an endoscope and an endoscope power receiving method compatible with video processors with different numbers of power supply system.

Hereinafter, an embodiment of the disclosure will be described in detail with reference to the accompanying drawings.

Note that drawings based on the embodiment are schematic and a relationship between the thickness and width of each component, a ratio of thickness of each component, relative angles or the like among the respective components are different from the actual relationship, thickness ratio, relative angles or the like. Parts with different dimensional relationships and ratios among the drawings are also included.

Figure 1:
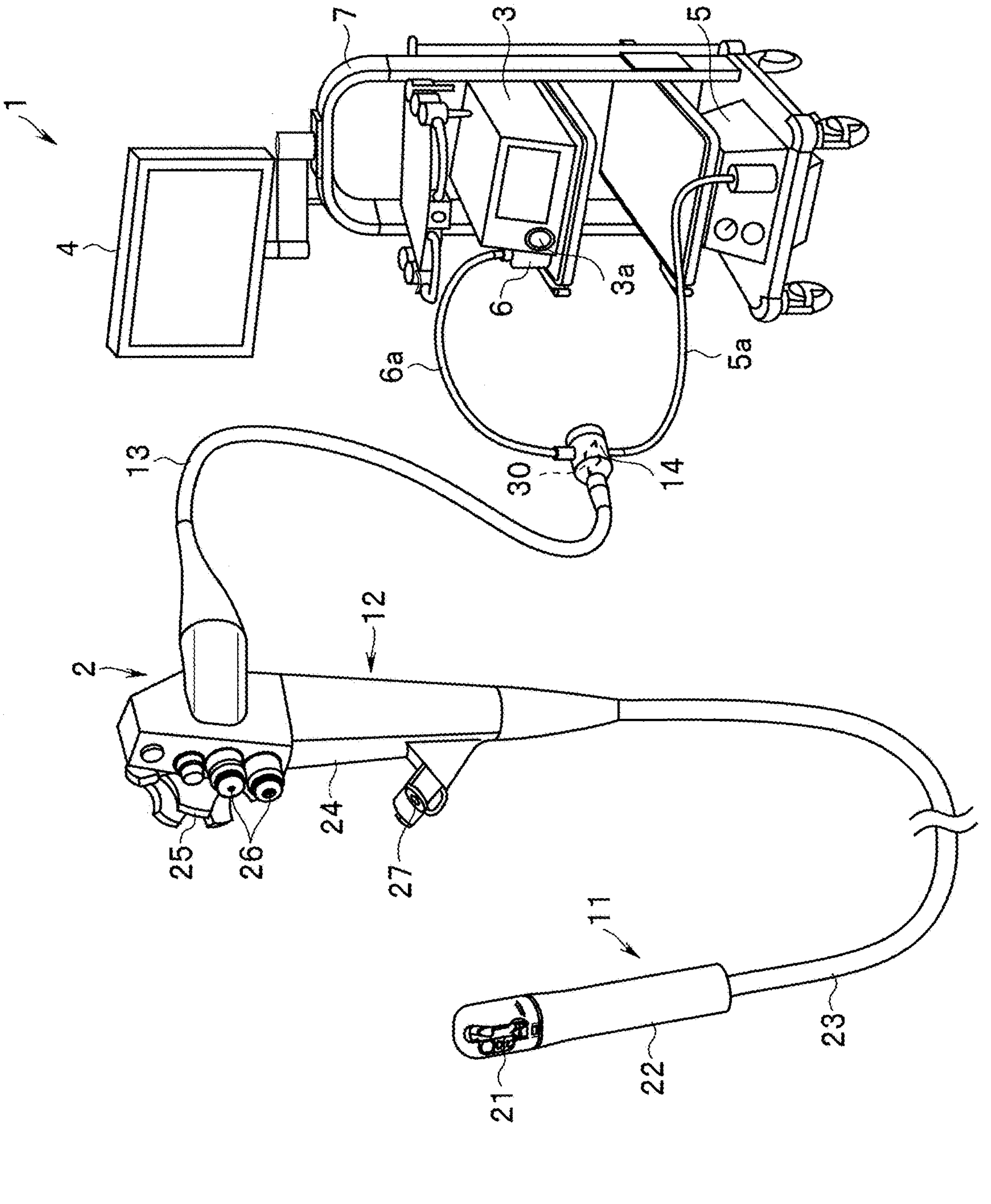
FIG. 1 is an overall configuration diagram illustrating an example of an overall configuration of an endoscope system according to an embodiment.

FIG. 1 is an overall configuration diagram illustrating an example of an overall configuration of an endoscope system according to an embodiment.

An endoscope system 1 is equipped with, for example, an endoscope 2, a video processor 3, a monitor 4, a suction pump 5 and a water feeding tank 6. The video processor 3, the monitor 4 and the suction pump 5 are placed on or fixed to a cart 7 as shown in FIG. 1. The water feeding tank 6 is attached to, for example, a side of the video processor 3. The endoscope system 1 is placed in an examination room where a subject is, for example, examined or treated.

The endoscope 2 is provided with, for example, an insertion portion 11 to be inserted into an observation target region of a subject, an operation portion 12 coupled to a proximal end portion of the insertion portion 11, a universal cable 13 that extends from a side of the operation portion 12 and a connector 14 provided at an extending end portion of the universal cable 13. The subject is assumed to be lumen of a living body such as a human or an animal. However, the subject can also be a non-living body such as a machine or a building.

The insertion portion 11 includes a distal end portion 21, for example, on a distal end side and a flexible bending portion 22 is coupled to a proximal end portion of the distal end portion 21. Furthermore, a long flexible tube portion 23 formed of a flexible tubular member is coupled to a proximal end portion of the bending portion 22.

For example, an image pickup unit, a distal end portion of a light guide, a distal-end-side opening of a treatment instrument channel and the like are placed at the distal end portion 21. The image pickup unit includes an image pickup optical system and an image sensor. The image pickup optical system forms an optical image of the subject on the image sensor. The image sensor photoelectrically converts (picks up an image of) the optical image of the subject and generates a video signal.

The image sensor includes but is not limited to a CCD (charge coupled device) image sensor, a CMOS (complementary metal-oxide semiconductor) image sensor or the like.

The bending portion 22 is a bendable part, for example, in two directions or four directions (up, down, left, right).

The flexible tube portion 23 is a flexible tube. Note that the endoscope 2 is an example of a flexible endoscope including the flexible tube portion 23. However, the endoscope 2 may also be a rigid endoscope with a portion corresponding to the flexible tube portion 23 being rigid.

The operation portion 12 is a region for a user to operate the endoscope 2. The operation portion 12 is disposed on the proximal end side of the insertion portion 11. The operation portion 12 is provided with, for example, a grasping portion 24, a bending operation knob 25, a plurality of operation buttons 26 and a treatment instrument insertion opening 27.

The grasping portion 24 is a region for the user to grasp the endoscope 2 with the palm of the hand.

The bending operation knob 25 is an operation device to operate the bending of the bending portion 22. The bending operation knob 25 is operated using, for example, the thumb of the hand grasping the grasping portion 24. When the bending operation knob 25 is operated, a bending operation wire is towed and the bending portion 22 is bent.

When the bending portion 22 is bent, a direction of the distal end portion 21 is changed. As a result, an image pickup direction by the image sensor and an irradiation direction of illumination light from the light guide are changed. The bending portion 22 is also bent to improve insertability of the insertion portion 11 into the subject.

The plurality of operation buttons 26 include, for example, an air/water feeding button, a suction button and a button related to image pickup. The air/water feeding button is a button for operation to feed air/water to an observation window provided on a distal end face of the image pickup unit at the distal end portion 21. The observation window is cleaned by water feeding and a liquid after cleaning is wiped off by air feeding. Air feeding and water feeding are done via air/water feeding channels (not shown).

The suction button is a button operated to suction the interior of the subject from the distal end portion 21. Suctioning from within the subject is performed via, for example, a suction channel. When the suctioning operation is performed, a liquid, a mucous membrane or the like is suctioned from within the subject.

Examples of the button related to image pickup include a button switch for release operation.

The treatment instrument insertion opening 27 is an opening on the proximal end side of the treatment instrument channel. A treatment instrument such as forceps is inserted inside the treatment instrument channel from the treatment instrument insertion opening 27. The distal end portion of the treatment instrument protrudes from an opening on the distal end side of the treatment instrument channel. Various kinds of treatment are given to the subject through the distal end portion of the protruding treatment instrument.

The connector 14 provided at the extending end of the universal cable 13 is connected to the video processor 3. More specifically, the connector 14 is connected to a connector receptacle 3*a* of the video processor 3. The connector 14 is equipped with an endoscope circuit board 30 configured to switch between connection targets depending on the number of power supply systems of the connected video processor 3. There are three types of the video processors 3: a first type having only a first power supply as a power supply, a second type having the first power supply and a second power supply as power supplies, and a third type having the first power supply, the second power supply, and a third power supply as power supplies. Note that a more detailed configuration of the endoscope circuit board 30 will be described later using FIG. 4.

The video processor 3 controls the entire endoscope system 1 including the endoscope 2, the monitor 4, the suction pump 5 or the like. The video processor 3 supplies power to the endoscope 2 and receives electric signals from the endoscope 2. In the example shown in FIG. 1, the video processor 3 is a video processor with a built-in light source (video processor with a built-in light source) and supplies illumination light to the endoscope 2. Note that the video processor 3 may be a separate entity from the light source apparatus.

The video processor 3 is provided with a light-emitting device as a light source such as an LED (light emitting diode) light source, a laser light source or a xenon light source. Connecting the connector 14 to the video processor 3 enables illumination light to be transmitted from the light source to the light guide.

Illumination light incident on a proximal end face of the light guide from the video processor 3 is transmitted (guided) by the light guide. The transmitted illumination light is radiated to the subject from the distal end face of the light guide disposed at the distal end portion 21 of the insertion portion 11.

The video processor 3 transmits a drive signal to drive the image sensor via a signal line. The video signal outputted from the image sensor is transmitted to the video processor 3 via the signal line.

The video processor 3 performs image processing on the video signal acquired by the image sensor and generates a displayable image signal. The video processor 3 may superimpose character information or the like on the image signal if necessary. The video processor 3 outputs the image signal to the monitor 4.

The monitor 4 receives the image signal from the video processor 3 and displays images including an endoscope image.

The suction pump 5 is connected to the connector 14 using a suction tube 5*a*. The connector 14 connects the suction tube 5*a* to a suction channel inside the endoscope 2. The suction pump 5 is used to suction a liquid, mucous membrane or the like from the subject.

The water feeding tank 6 is connected to the connector 14 of the endoscope 2 using an air/water feeding tube 6*a*. The connector 14 connects the air/water feeding tube 6*a* to the air/water feeding channel inside the endoscope 2.

The water feeding tank 6 is a tank to store a liquid such as a physiological salt solution. Sending a pressurized gas to the water feeding tank 6 from the air/water feeding pump inside the video processor 3 causes the liquid in the water feeding tank 6 to be sent to the air/water feeding channel.

The video processor 3 controls the entire endoscope system 1 including the endoscope 2, the monitor 4, the suction pump 5, the water feeding tank 6 or the like.

Figure 2:
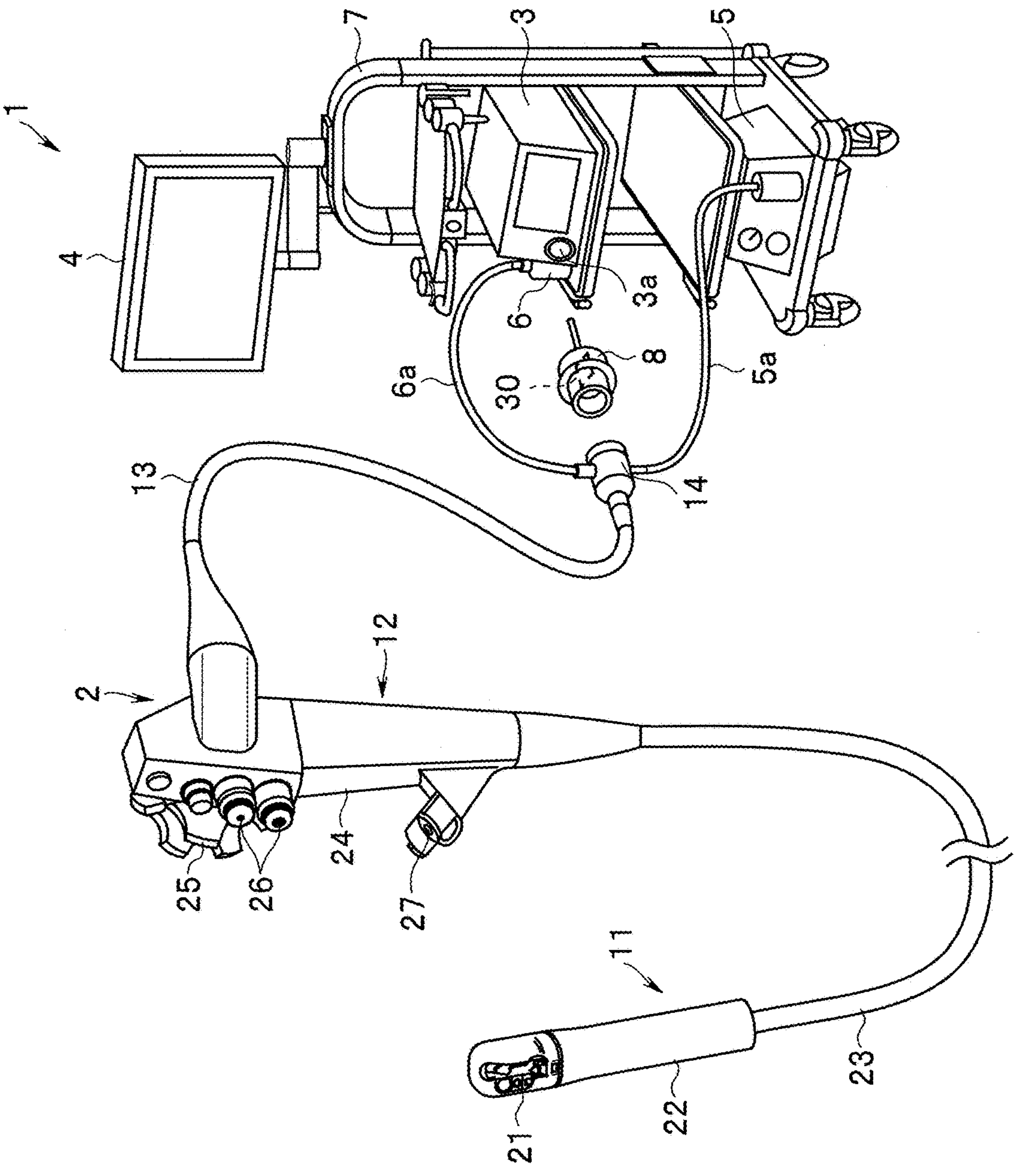
FIG. 2 is an overall configuration diagram illustrating another example of the overall configuration of the endoscope system according to the embodiment.

Note that the configuration of the endoscope system 1 is not limited to the configuration shown in FIG. 1. FIG. 2 is an overall configuration diagram illustrating another example of the overall configuration of the endoscope system according to the embodiment. Note that components in FIG. 2 similar to the components in FIG. 1 are given identical reference numerals and description is omitted.

As shown in FIG. 2, the endoscope 2 can also be connected to the video processor 3 via an adapter 8. The adapter 8 includes the endoscope circuit board 30 configured to switch between connection targets depending on the number of power supply systems of the connected video processor 3. In other words, the endoscope circuit board 30 is attachable to and detachable from a body of the endoscope 2.

Figure 3:
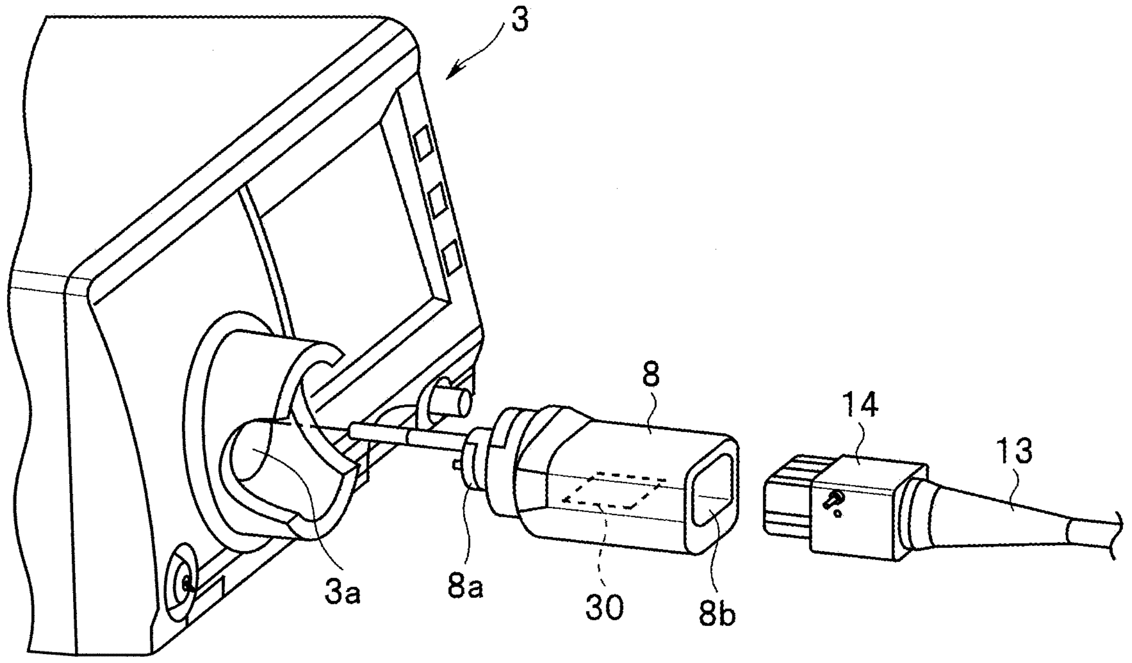
FIG. 3 is a perspective view illustrating a configuration of a part connecting an endoscope and a video processor via an adapter.

FIG. 3 is a perspective view illustrating a configuration of a part connecting the endoscope and the video processor via the adapter.

The adapter 8 is provided with a connector 8*a* connected to the connector receptacle 3*a* of the video processor 3 on one end side. The adapter 8 is also provided with a connector receptacle 8*b* connected to the connector 14 of the endoscope 2 on the other end side. In other words, the connector 8*b* has a configuration compatible with the connector 14 of the endoscope 2. The endoscope circuit board 30 is provided inside the adapter 8. Specifically, the endoscope circuit board 30 is interposed between the connector 8*a* and the connector 8*b*.

Figure 4:
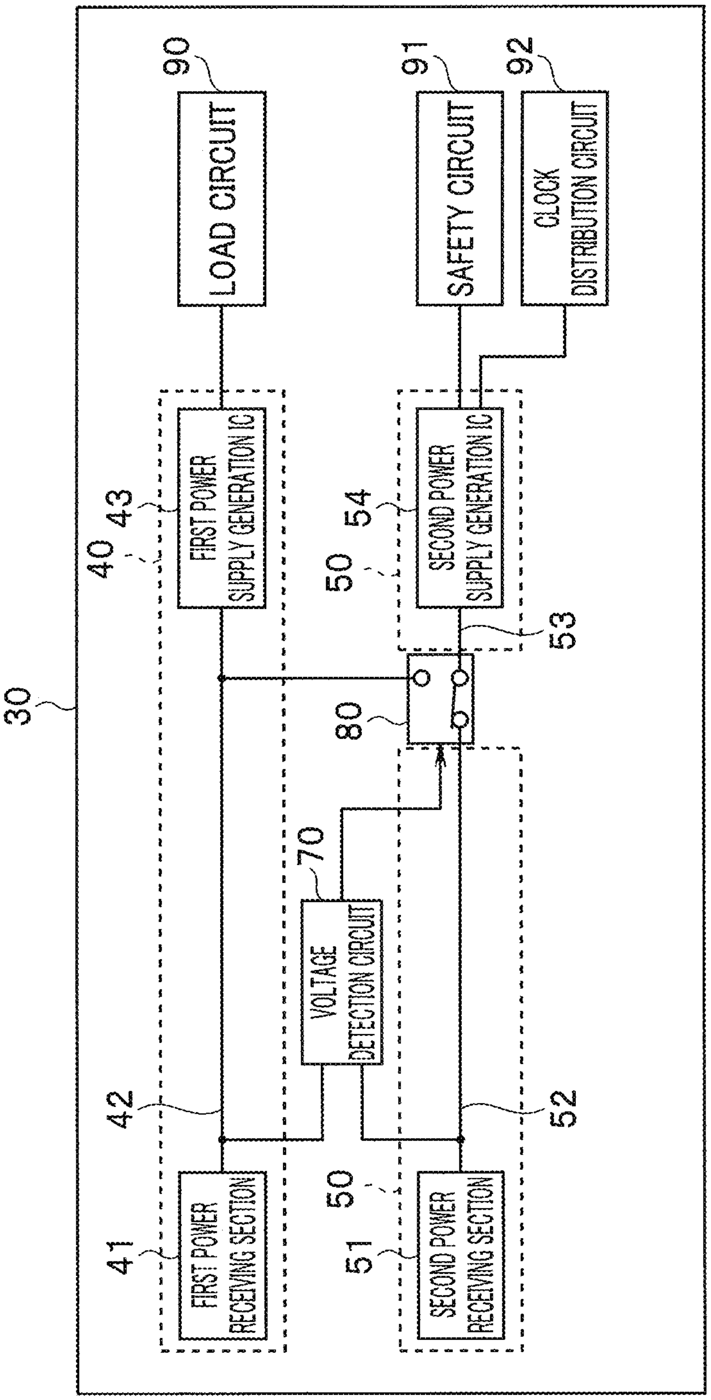
FIG. 4 is a block diagram illustrating an example of a configuration of an endoscope circuit board.

FIG. 4 is a block diagram illustrating an example of a configuration of the endoscope circuit board.

The endoscope circuit board 30 is provided with a first power supply system 40, a second power supply system 50, a voltage detection circuit 70, a first switch 80, a load circuit 90, a safety circuit 91, and a clock distribution circuit 92. The first power supply system 40 includes a first power receiving section 41, a first electric wire 42 and a first power supply generation IC 43 (a first power supply circuit).

Power is supplied to the first power receiving section 41 from the connected video processor 3. The first power receiving section 41 receives the power supplied from the video processor 3. Power is supplied to the first power receiving section 41 no matter whether the number of power supply systems of the connected video processor 3 is one or three. For example, the first power receiving section 41 may be an electrical contact of the video processor 3.

The first electric wire 42 connects the first power receiving section 41 and the first power supply generation IC 43.

The first power supply generation IC 43 generates a first power supply from the power supplied via the first electric wire 42 and supplies the first power supply to, for example, the load circuit 90.

The second power supply system 50 includes a second power receiving section 51, a second electric wire 52, a third electric wire 53 and a second power supply generation IC 54 (a second power supply circuit).

Power is supplied to the second power receiving section 51 from the connected video processor 3. The second power receiving section 51 receives the power supplied from the video processor 3. However, no power is supplied to the second power receiving section 51 if the number of power supply systems of the connected video processor 3 is one, whereas power is supplied if the number of power supply systems is three. For example, the second power receiving section 51 may be an electrical contact of the video processor 3.

The second electric wire 52 is connected to the second power receiving section 51. The third electric wire 53 is connected to the second power supply generation IC 54.

The second power supply generation IC 54 generates a second power supply from the power supplied via the first electric wire 42 and the third electric wire 53 or from the power supplied via the second electric wire 52 and the third electric wire 53, and supplies the second power supply to, for example, the safety circuit 91 and the clock distribution circuit 92.

One end (input end) of the voltage detection circuit 70 is connected to the first electric wire 42 and the second electric wire 52, and the other end (output end) is connected to the first switch 80. In other words, the power received by the first power receiving section 41 and the second power receiving section 51 is supplied to the voltage detection circuit 70. Only when power is supplied from the first power receiving section 41 with no power being supplied from the second power receiving section 51, the voltage detection circuit 70 sends signals to the first switch 80.

The first switch 80 is connected to the third electric wire 53 so as to be able to switch between a state in which the second electric wire 52 and the third electric wire 53 are electrically connected, and a state in which the first electric wire 42 and the third electric wire 53 are electrically connected.

The first switch 80 makes the first electric wire 42 and the third electric wire 53 conductive when signals are sent from the voltage detection circuit 70.

In this way, when only the first power receiving section 41 receives power, the power received by the first power receiving section 41 is supplied to the first power supply generation IC 43 and the second power supply generation IC 54.

On the other hand, except when power is supplied from the first power receiving section 41 with no power being supplied from the second power receiving section 51, the voltage detection circuit 70 does not send any signal to the first switch 80. For example, when the first power receiving section 41 and the second power receiving section 51 receive power and power is supplied from the first power receiving section 41 and the second power receiving section 51, the voltage detection circuit 70 sends no signal to the first switch 80.

When no signal is sent from the voltage detection circuit 70, the first switch 80 makes the second electric wire 52 and the third electric wire 53 conductive.

In this way, when the first power receiving section 41 and the second power receiving section 51 receive power, the power received by the first power receiving section 41 is supplied to the first power supply generation IC 43, the power received by the second power receiving section 51 is supplied to the second power supply generation IC 54.

Figure 5:
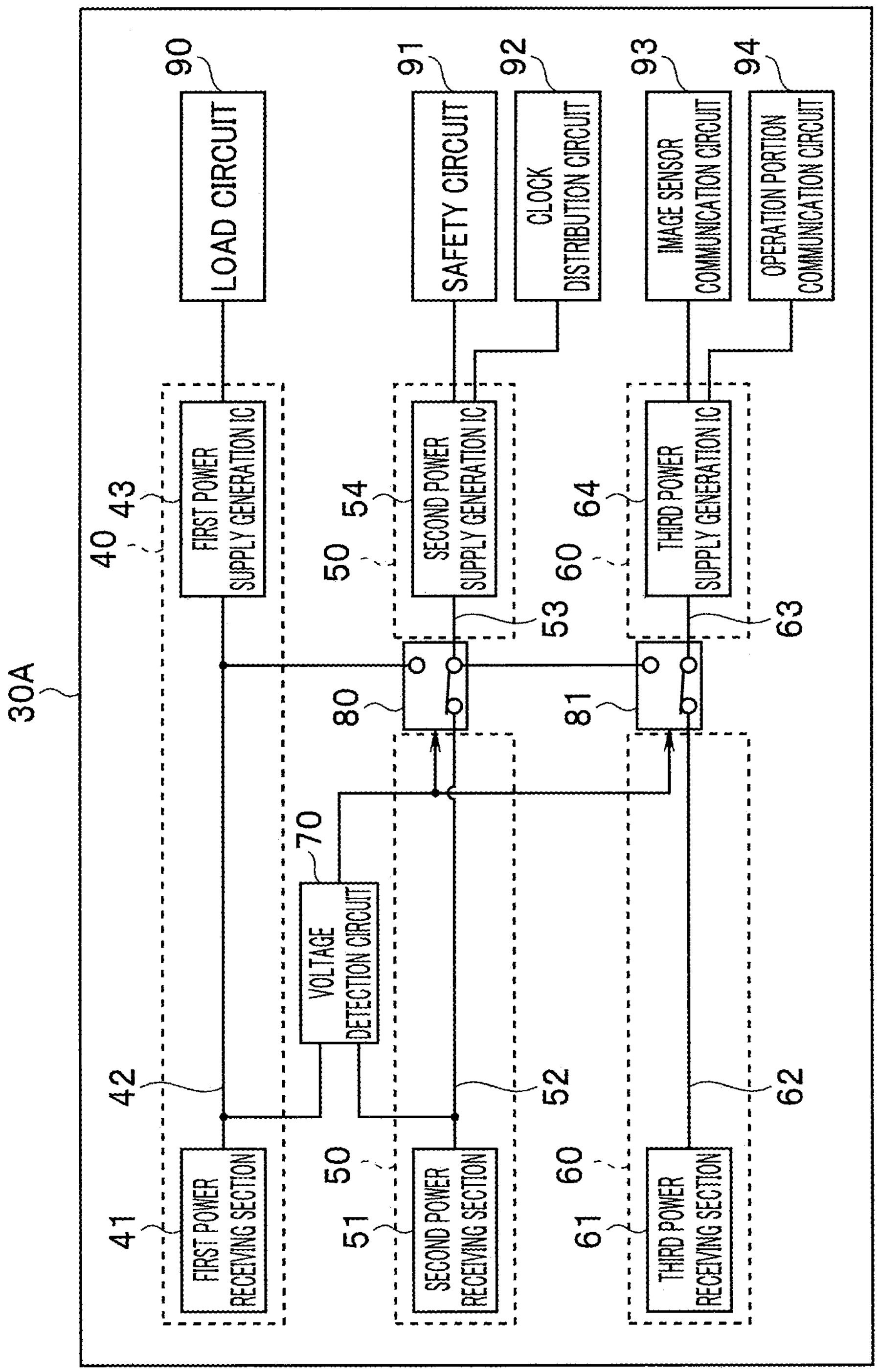
FIG. 5 is a block diagram illustrating another example of the configuration of the endoscope circuit board.

FIG. 5 is a block diagram illustrating another example of the configuration of the endoscope circuit board.

The endoscope circuit board 30A shown in FIG. 5 is configured by the endoscope circuit board 30 shown in FIG. 4 with the addition of a third power supply system 60, a second switch 81, an image sensor communication circuit 93, and an operation portion communication circuit 94.

The third power supply system 60 includes a third power receiving section 61, a fourth electric wire 62, a fifth electric wire 63 and a third power supply generation IC 64 (a thid power supply circuit).

Power is supplied to the third power receiving section 61 from the connected video processor 3. The third power receiving section 61 receives the power supplied from the video processor 3. However, no power is supplied to the third power receiving section 61 if the number of power supply systems of the connected video processor 3 is one, whereas power is supplied if the number of power supply systems is three. For example, the third power receiving section 61 may be an electrical contact of the video processor 3.

The fourth electric wire 62 is connected to the third power receiving section 61 and the fifth electric wire 63 is connected to the third power supply generation IC 64.

The third power supply generation IC 64 generates a third power supply from the power supplied via the first electric wire 42 and the fifth electric wire 63 or from the power supplied via the fourth electric wire 62 and the fifth electric wire 63, and supplies the third power supply to, for example, the image sensor communication circuit 93 and the operation portion communication circuit 94.

One end (input end) of the voltage detection circuit 70 is connected to the first electric wire 42 and the second electric wire 52, and the other end (output end) is connected to the first switch 80 and the second switch 81. Only when power is supplied from the first power receiving section 41 with no power being supplied from the second power receiving section 51, the voltage detection circuit 70 sends signals to the first switch 80 and the second switch 81.

The second switch 81 is connected to the fifth electric wire 63 so as to be able to switch between a state in which the fourth electric wire 62 and the fifth electric wire 63 are electrically connected and a state in which the first electric wire 42 and the fifth electric wire 63 are electrically connected via the first switch 80.

The first switch 80 makes the first electric wire 42 and the third electric wire 53 conductive when signals are sent from the voltage detection circuit 70. The second switch 81 makes the first electric wire 42 and the fifth electric wire 63 conductive when signals are sent from the voltage detection circuit 70.

In this way, when only the first power receiving section 41 receives power, the power received by the first power receiving section 41 is supplied to the first power supply generation IC 43, the second power supply generation IC 54 and the third power supply generation IC 64.

On the other hand, except when power is supplied from the first power receiving section 41 with no power being supplied from the second power receiving section 51, the voltage detection circuit 70 does not send any signal to the first switch 80 and the second switch 81. For example, when all the first power receiving section 41, the second power receiving section 51 and the third power receiving section 61 receive power and power is supplied from the first power receiving section 41 and the second power receiving section 51, the voltage detection circuit 70 sends no signal to either the first switch 80 or the second switch 81.

When no signal is sent from the voltage detection circuit 70, the first switch 80 makes the second electric wire 52 and the third electric wire 53 conductive. When no signal is sent from the voltage detection circuit 70, the second switch 81 makes the fourth electric wire 62 and the fifth electric wire 63 conductive.

In this way, when all the first power receiving section 41, the second power receiving section 51 and the third power receiving section 61 receive power, the power received by the first power receiving section 41 is supplied to the first power supply generation IC 43, the power received by the second power receiving section 51 is supplied to the second power supply generation IC 54, and the power received by the third power receiving section 61 is supplied to the third power supply generation IC 64.

Figure 6:
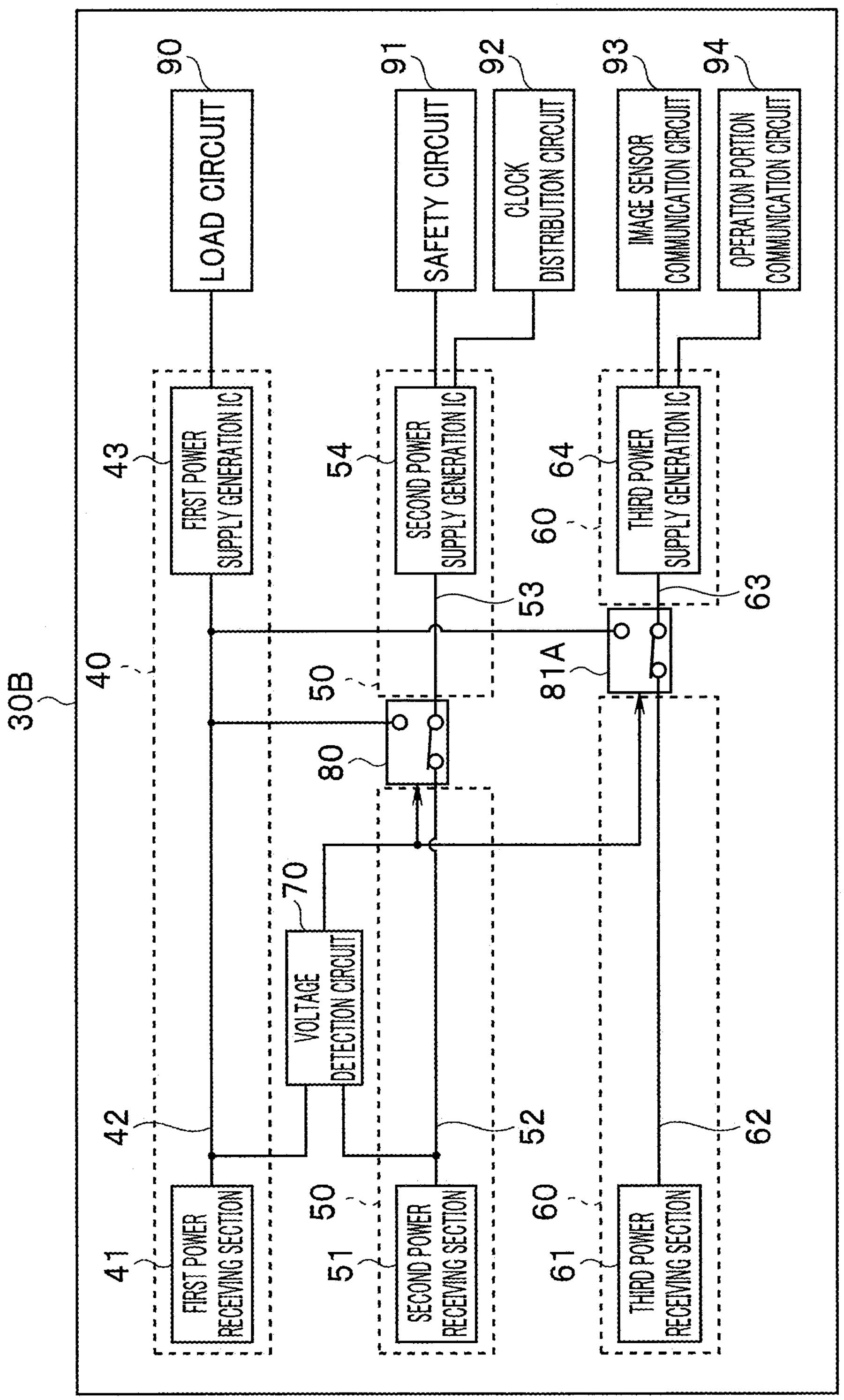
FIG. 6 is a block diagram illustrating yet another example of the configuration of the endoscope circuit board.

FIG. 6 is a block diagram illustrating another example of the configuration of the endoscope circuit board.

An endoscope circuit board 30B shown in FIG. 6 is provided with a second switch 81A instead of the second switch 81 of the endoscope circuit board 30A shown in FIG. 5.

The second switch 81 shown in FIG. 5 connects the first electric wire 42 and the fifth electric wire 63 via the first switch 80.

On the other hand, the second switch 81A shown in FIG. 6 directly electrically connects the first electric wire 42 and the fifth electric wire 63 without going through the first switch 80. The rest of the configuration is similar to the configuration of the endoscope circuit board 30A.

Figure 7:
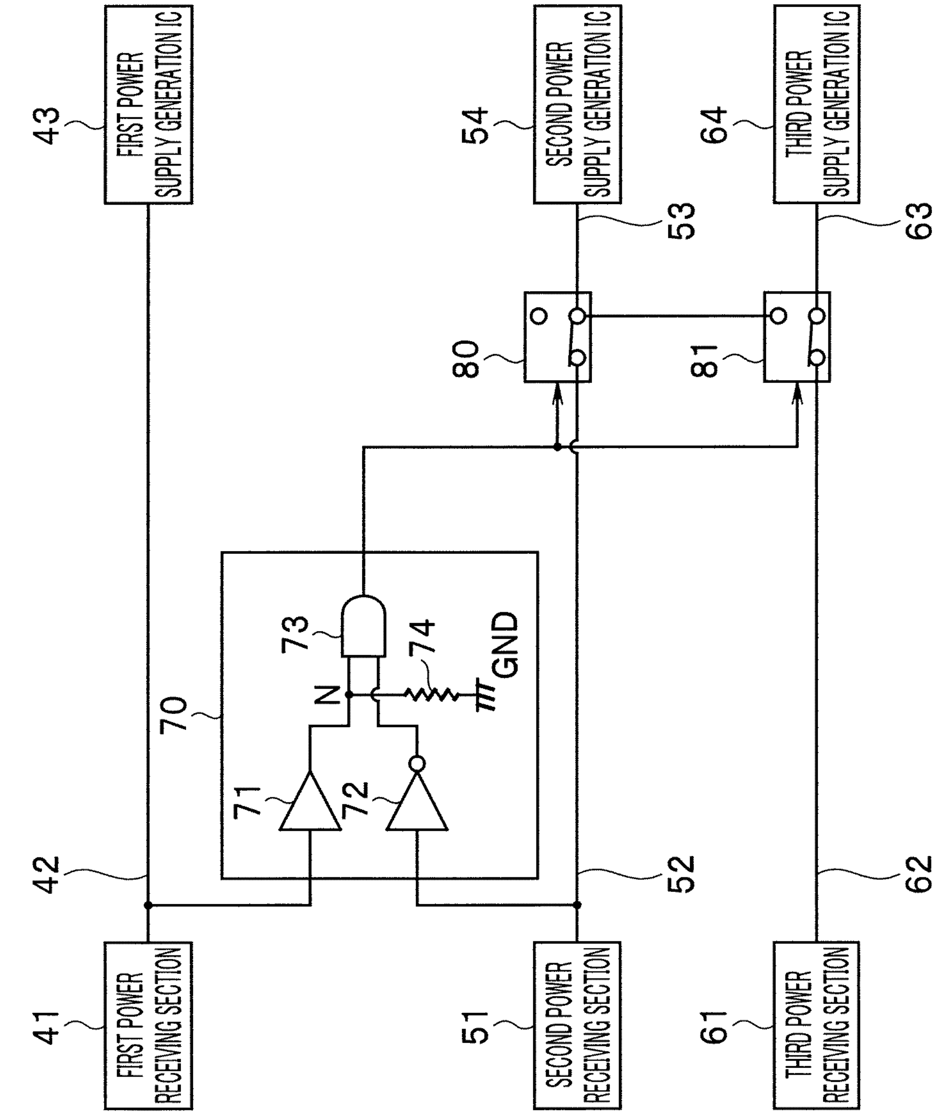
FIG. 7 is a block diagram illustrating a detailed configuration of a voltage detection circuit.

FIG. 7 is a block diagram illustrating a detailed configuration of the voltage detection circuit. Note that FIG. 7 shows only a configuration of part of the endoscope circuit board 30.

The voltage detection circuit 70 is provided with a buffer circuit 71, an inverter circuit 72, an AND circuit 73 and a discharge resistor 74.

The buffer circuit 71 is configured to delay a signal from the first power receiving section 41 and output the signal to the AND circuit 73.

The inverter circuit 72 is configured to invert the signal from the second power receiving section 51 and output the signal to the AND circuit 73.

The AND circuit 73 calculates a logical product of an output signal of the buffer circuit 71 and an output signal of the inverter circuit 72, and outputs a calculation result as an output signal to the first switch 80 and the second switch 81. The buffer circuit 71, the inverter circuit 72, and the AND circuit 73 configure a delay mechanism.

The discharge resistor 74 is connected between a node N between the buffer circuit 71 and the AND circuit 73, and a ground GND, and the discharge resistor 74 discharges an output signal of the buffer circuit 71. The discharge resistor 74 configures a discharge mechanism.

FIG. 8 is a diagram illustrating a truth table of the voltage detection circuit. FIG. 8 represents an example that the number of power supply system is one or three. However, more than two power supply systems can be used instead of three power supply systems.

When an H-level signal is inputted from the first power receiving section 41 to the voltage detection circuit 70, the signal is delayed by the buffer circuit 71 and an H-level signal is outputted to the AND circuit 73. When an L-level signal is inputted from the second power receiving section 51 to the voltage detection circuit 70, the signal is inverted by the inverter circuit 72 and an H-level signal is outputted to the AND circuit 73.

When the outputs of the buffer circuit 71 and the inverter circuit 72 are H level, the AND circuit 73 outputs an H-level signal. On the other hand, when the outputs of the buffer circuit 71 and the inverter circuit 72 are a combination other than an H level, the AND circuit 73 outputs an L-level signal.

Thus, as shown in FIG. 8, an H-level signal is outputted from the voltage detection circuit 70 only when an H-level signal is inputted from the first power receiving section 41 and an L-level signal is inputted from the second power receiving section 51.

Here, functions of the buffer circuit 71 will be described.

Normally, the video processor 3 with three power supply systems includes a first power supply, a second power supply and a third power supply. Power from the first power supply, the second power supply and the third power supply is supplied to the first power receiving section 41, the second power receiving section 51 and the third power receiving section 61 respectively. When power is turned on, the video processor 3 with such three power supply systems follows a power supply sequence of turning on the first power supply and the second power supply simultaneously, and then turning on the third power supply.

Although the power supply sequence is such that the first power supply and the second power supply are turned on simultaneously, due to manufacturing variations or the like, the actual rise time of the first power supply and the second power supply may deviate or due to variations in wiring delays or the like, signals inputted to the voltage detection circuit 70 may deviate.

Figure 9A:
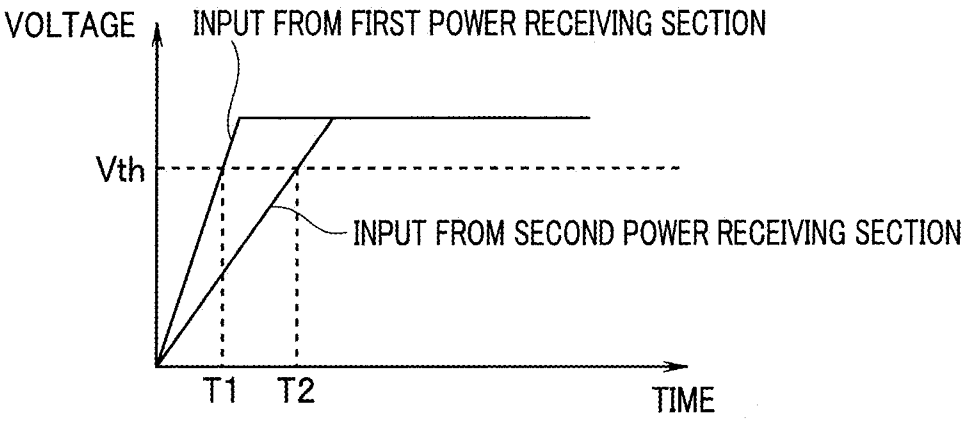
FIG. 9A is a diagram illustrating an example of signal change with no delay function.
Figure 9B:
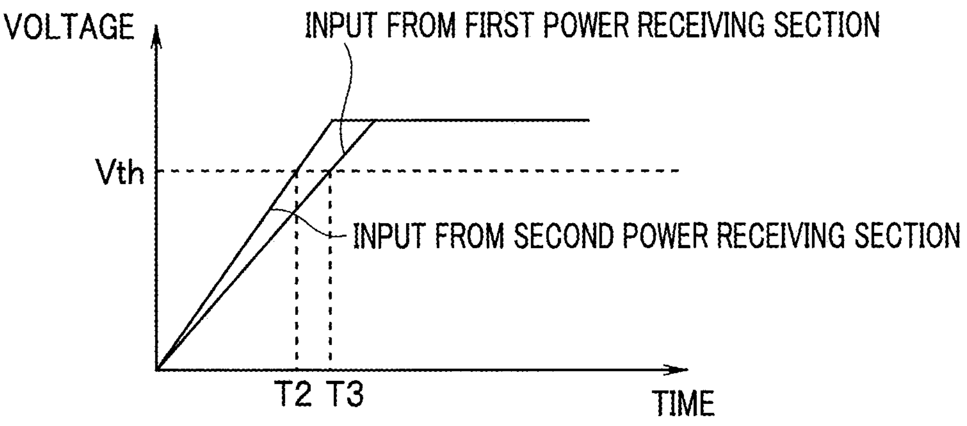
FIG. 9B is a diagram illustrating an example of signal change with the delay function.

FIG. 9A is a diagram illustrating an example of signal change with no delay function. FIG. 9B is a diagram illustrating an example of signal change with the delay function.

As described above, since the first power supply and the second power supply of the video processor 3 are turned on simultaneously, signals inputted to the voltage detection circuit 70 from the first power receiving section 41 and the second power receiving section 51 should also rise simultaneously.

However, due to manufacturing variations or the like, a signal inputted from the first power receiving section 41 may rise before a signal inputted from the second power receiving section 51 as shown in FIG. 9A.

Until a time point T1, the signal inputted from the first power receiving section 41 is determined to be an L level and the signal inputted from the second power receiving section 51 is determined to be an L level. In this case, as shown in the truth table in FIG. 8, the number of power supply systems is determined to be three and the voltage detection circuit 70 outputs L-level signals to the first switch 80 and the second switch 81.

On the other hand, from the time point T1 until a time point T2, the signal inputted from the first power receiving section 41 is determined to be an H level, the signal inputted from the second power receiving section 51 is determined to be an L level. In this case, as shown in the truth table in FIG. 8, the number of power supply systems is determined to be one, and the voltage detection circuit 70 outputs H-level signals to the first switch 80 and the second switch 81.

After the time point T2, the signal inputted from the first power receiving section 41 is determined to be an H level and the signal inputted from the second power receiving section 51 is determined to be an H level. In this case, as shown in the truth table in FIG. 8, the number of power supply systems is determined to be three and the voltage detection circuit 70 outputs L-level signals to the first switch 80 and the second switch 81.

In other words, the output of the voltage detection circuit 70 changes in order of an L level, an H level and an L level, which causes switching between the first switch 80 and the second switch 81 to take place. In order to prevent such switching between the switches, the buffer circuit 71 provides a sufficiently large delay with respect to the inverter circuit 72.

As shown in FIG. 9B, the delay in the buffer circuit 71 causes the signal inputted from the first power receiving section 41 to rise later than the signal inputted from the second power receiving section 51. Until the time point T2, this causes the signal inputted from the first power receiving section 41 to be determined to be an L level and causes the signal inputted from the second power receiving section 51 to be determined to be an L level. On the other hand, from the time point T2 until a time point T3, the signal inputted from the first power receiving section 41 is determined to be an L level and the signal inputted from the second power receiving section 51 is determined to be an H level. Furthermore, after the time point T3, the signal inputted from the first power receiving section 41 is determined to be an H level, and the signal inputted from the second power receiving section 51 is determined to be an H level.

In this way, when the signals are inputted from the first power receiving section 41 and the second power receiving section 51, the number of power supply systems is determined to be three in both cases as shown in the truth table in FIG. 8 and the voltage detection circuit 70 outputs L-level signals to the first switch 80 and the second switch 81. In this way, by ensuring that the input from the first power receiving section 41 rises after the input from the second power receiving section 51, it is possible to prevent unnecessary switching between the switches.

Next, functions of the discharge resistor 74 will be described.

Normally, when turning on the power supplies, the video processor 3 with three power supply systems follows a power supply sequence such that the third power supply falls, and then the first power supply and the second power supply fall simultaneously.

Although the power supply sequence is such that the first power supply and the second power supply fall simultaneously, due to manufacturing variations or the like, the actual fall times of the first power supply and the second power supply may deviate or due to variations in wiring delays or the like, signals inputted to the voltage detection circuit 70 may deviate.

Figure 10A:
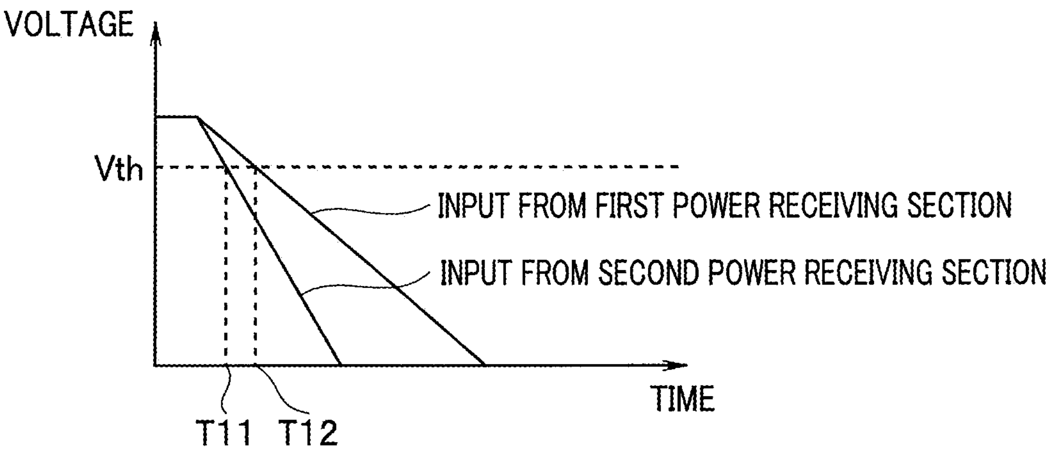
FIG. 10A is a diagram illustrating an example of signal change with no discharge function.
Figure 10B:
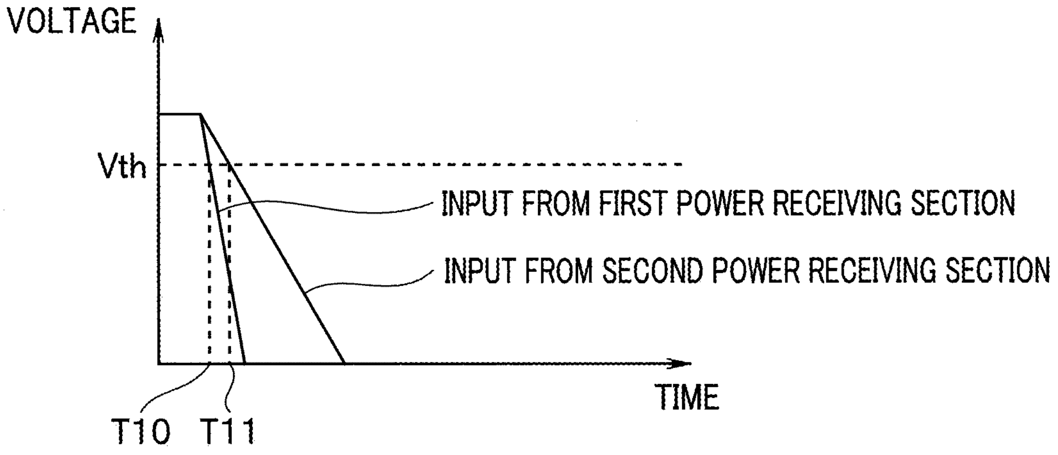
FIG. 10B is a diagram illustrating an example of signal change with the discharge function.

FIG. 10A is a diagram illustrating an example of signal change in a case with no discharge function. FIG. 10B is a diagram illustrating an example of signal change in a case with the discharge function.

As described above, since the first power supply and the second power supply of the video processor 3 fall simultaneously, the signals inputted to the voltage detection circuit 70 from the first power receiving section 41 and the second power receiving section 51 should also fall simultaneously.

However, due to manufacturing variations or the like, the signals inputted from the first power receiving section 41 may fall after the signals inputted from the second power receiving section 51 as shown in FIG. 10A.

Until a time point T11, the signal inputted from first power receiving section 41 is determined to be an H level and the signal inputted from the second power receiving section 51 is determined to be an H level. In this case, as shown in the truth table in FIG. 8, the number of power supply systems is determined to be three, and the voltage detection circuit 70 outputs an L-level signals to the first switch 80 and the second switch 81.

On the other hand, from the time point T11 until a time point T12, the signal inputted from the first power receiving section 41 is determined to be an H level and the signal inputted from the second power receiving section 51 is determined to be an L level. In this case, as shown in the truth table in FIG. 8, the number of power supply systems is determined to be one, and the voltage detection circuit 70 outputs H-level signals to the first switch 80 and the second switch 81.

After the time point T12, the signal inputted from the first power receiving section 41 is determined to be an L level and the signal inputted from the second power receiving section 51 is determined to be an L level. In this case, as shown in the truth table in FIG. 8, the number of power supply systems is determined to be three and the voltage detection circuit 70 outputs L-level signals to the first switch 80 and the second switch 81.

In other words, the output of the voltage detection circuit 70 is switched in order of an L level, an H level and an L level, causing switching between the first switch 80 and the second switch 81. In order to prevent such switching between the switches, the discharge resistor 74 has a function of discharging the output of the buffer circuit 71 and causing the signal to quickly fall to an L level.

As shown in FIG. 10B, the discharge resistor 74 discharges the signal inputted from the first power receiving section 41 to thereby cause the signal inputted from the first power receiving section 41 to fall before the signal inputted from the second power receiving section 51.

Thus, until the time point T10, the signal inputted from the first power receiving section 41 is determined to be an H level and the signal inputted from the second power receiving section 51 is determined to be an H level. From the time point T10 until the time point T11, the signal inputted from the first power receiving section 41 is determined to be an L level and the signal inputted from the second power receiving section 51 is determined to be an H level. Furthermore, after the time point T12, the signal inputted from the first power receiving section 41 is determined to be an L level and the signal inputted from the second power receiving section 51 is determined to be an L level.

In this way, when signals are inputted from the first power receiving section 41 and the second power receiving section 51, the number of power supply systems is determined to be three in both cases as shown in the truth table in FIG. 8, and the voltage detection circuit 70 outputs L-level signals to the first switch 80 and the second switch 81. Thus, by causing the input from the second power receiving section 51 to fall after the input from the first power receiving section 41, it is possible to prevent unnecessary switching between the switches.

Figure 11:
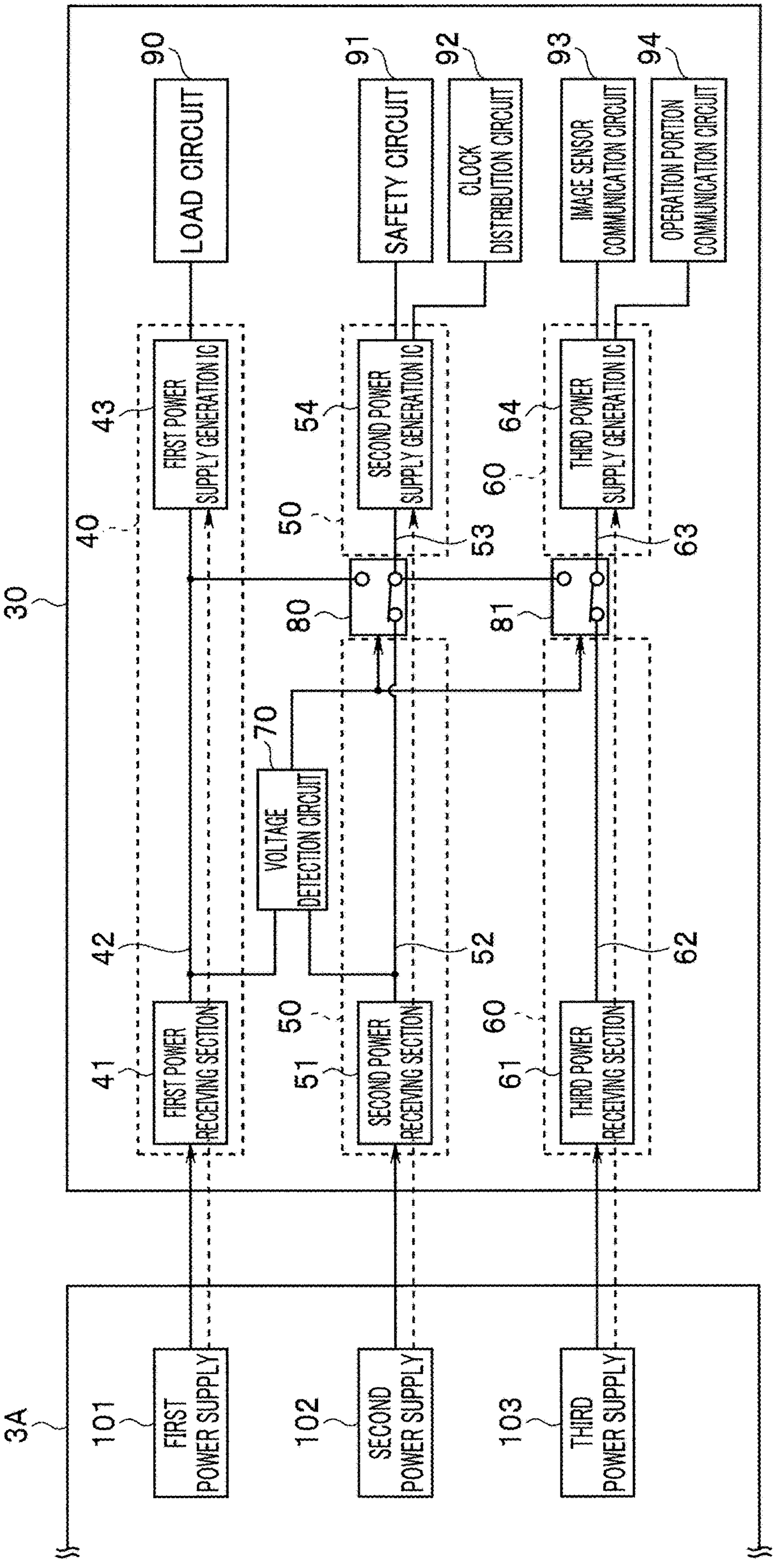
FIG. 11 is a block diagram illustrating an example of a configuration when the endoscope is connected to a video processor with three power supply systems.

FIG. 11 is a block diagram illustrating an example of a configuration when the endoscope is connected to a video processor with three power supply systems.

A video processor 3A with three power supply systems includes a first power supply 101, a second power supply 102 and a third power supply 103. When the endoscope 2 is connected to the video processor 3A, power is supplied from the first power supply 101, the second power supply 102 and the third power supply 103 to the first power receiving section 41, the second power receiving section 51 and the third power receiving section 61, respectively.

In this way, H-level signals are inputted to the voltage detection circuit 70 from the first power receiving section 41 and the second power receiving section 51. When the H-level signals are inputted from the first power receiving section 41 and the second power receiving section 51, the voltage detection circuit 70 outputs L-level signals to the first switch 80 and the second switch 81.

When the L-level signal is inputted, the first switch 80 connects the second electric wire 52 and the third electric wire 53. When the L-level signal is inputted, the second switch 81 connects the fourth electric wire 62 and the fifth electric wire 63.

As a result, power from the first power supply 101 is supplied to the first power supply generation IC 43, power from the second power supply 102 is supplied to the second power supply generation IC 54, and power from the third power supply 103 is supplied to the third power supply generation IC 64.

Figure 12:
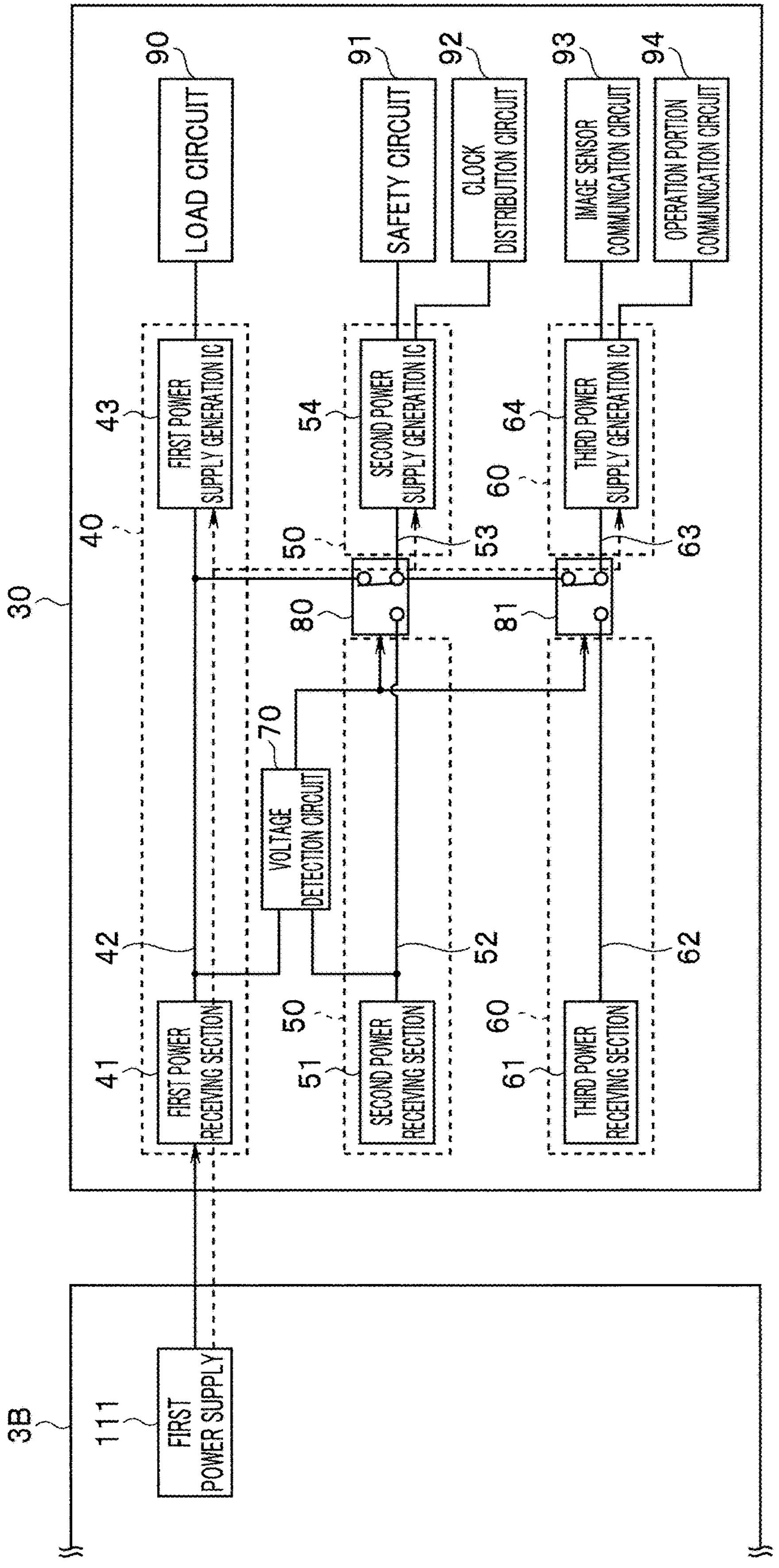
FIG. 12 is a block diagram illustrating an example of a configuration when the endoscope is connected to a video processor with one power supply system.

FIG. 12 is a block diagram illustrating an example of a configuration when the endoscope is connected to a video processor with one power supply system.

A video processor 3B with one power supply system includes a first power supply 111. When the endoscope 2 is connected to the video processor 3B, power is supplied to the first power receiving section 41 from the first power supply 111.

In this way, an H-level signal is inputted to the voltage detection circuit 70 from the first power receiving section 41. On the other hand, an L-level signal is inputted to the voltage detection circuit 70 from the second power receiving section 51. When the H level is inputted from the first power receiving section 41 and the L-level signal is inputted from the second power receiving section 51, the voltage detection circuit 70 outputs H-level signals to the first switch 80 and the second switch 81.

When the H-level signal is inputted, the first switch 80 connects the first electric wire 42 and the third electric wire 53. When the H-level signal is inputted, the second switch 81 connects the first electric wire 42 and the fifth electric wire 63 via the first switch 80.

As a result, power from a first power supply 111 is supplied to the first power supply generation IC 43, the second power supply generation IC 54 and the third power supply generation IC 64.

As described above, the endoscope 2 provided with the endoscope circuit board 30 can be adapted to video processors with different numbers of power supply systems, for example, an old video processor 3A with three power supply systems or a new video processor 3B with one power supply system.

The disclosure is not limited to the aforementioned embodiments or the like, and various modifications and alterations or the like may be made to the embodiments without changing the gist of the invention.

The invention claimed is:

1. An endoscope circuit board comprising:
- a first power supply system, the first power supply system comprising:
  - a first power receiving section,
  - a first power supply circuit, and
  - a first electric wire electrically connecting the first power receiving section and the first power supply circuit;
  - a second power supply system, the second power supply system comprising:
  - a second power receiving section,
  - a second electric wire electrically connected to the second power receiving section,
  - a second power supply circuit, and
  - a third electric wire;
- a first switch, the first switch being electrically connected to the third electric wire to switch between a first state in which the second electric wire and the third electric wire are electrically connected and a second state in which the first electric wire and the third electric wire are electrically connected; and
- a voltage detection circuit configured to: send a signal to the first switch only when power is supplied from the first power receiving section without any power being supplied from the second power receiving section;
- wherein when the first switch receives a signal from the voltage detection circuit, if only the first power receiving section receives power by causing the first electric wire and the third electric wire to electrically connect, the power received by the first power receiving section is supplied to the first power supply circuit and the second power supply circuit, and
- when each of the first power receiving section and the second power receiving section receive power, the power received by the first power receiving section is supplied to the first power supply circuit and the power received by the second power receiving section is supplied to the second power supply circuit.

2. The endoscope circuit board according to claim 1, the endoscope circuit board comprising:
- a third power supply system, the third power supply system comprising
  - a third power receiving section,
  - a fourth electric wire electrically connected to the third power receiving section,
  - a third power supply circuit, and
  - a fifth electric wire; and
- a second switch, wherein
- the second switch is electrically connected to the fifth electric wire to switch between a third state in which the fourth electric wire and the fifth electric wire are electrically conducting and a fifth state in which the first electric wire and the fifth electric wire are electrically conducting,
- the voltage detection circuit is configured to send signals to the first switch and the second switch only when power is supplied from the first power receiving section with no power being supplied from the second power receiving section,
- wherein when the second switch receives a signal from the voltage detection circuit, the second switch causes the first electric wire and the fifth electric wire to electrically connect,
- when only the first power receiving section receives power, the power received by the first power receiving section is supplied to the first power supply circuit, the second power supply circuit and the third power supply circuit, and
- when each of the first power receiving section, the second power receiving section and the third power receiving section receive power, the power received by the first power receiving section is supplied to the first power supply circuit and the power received by the second power receiving section is supplied to the second power supply circuit and the power received by the third power receiving section is supplied to the third power supply circuit.

3. The endoscope circuit board according to claim 2, wherein
- the voltage detection circuit comprises a delay mechanism, and
- the delay mechanism is configured to receive power from the first power receiving section a predetermined time after receiving power from the first power receiving section, whereas when the delay mechanism receives no power from the second power receiving section, the delay mechanism is configured to send signals to the first switch and the second switch.

4. The endoscope circuit board according to claim 2, wherein
- the voltage detection circuit comprises a discharge mechanism, and
- the discharge mechanism is configured to discharge power received by the first power receiving section.

5. The endoscope circuit board according to claim 2, wherein the voltage detection circuit comprises a buffer circuit electrically connected to the first power receiving section, an inverter circuit electrically connected to the second power receiving section, an AND circuit configured to calculate a logical product of output of the buffer circuit and output of the inverter circuit, and a discharge resistor provided between the buffer circuit and the AND circuit.

6. The endoscope circuit board according to claim 2, further comprising at least one of a safety circuit electrically connected to the second power supply circuit or a clock distribution circuit.

7. The endoscope circuit board according to claim 2, further comprising at least one of an image sensor communication circuit electrically connected to the third power supply circuit or an operation portion communication circuit.

8. An endoscope comprising the endoscope circuit board according to claim 1.

9. The endoscope according to claim 8, wherein the endoscope circuit board is placed in a connector provided at a distal end of a universal cable of a body of the endoscope.

10. The endoscope according to claim 8, wherein the endoscope circuit board is attachable to and detachable from a body of the endoscope.

11. The endoscope according to claim 10, further comprising an adapter attachable to and detachable from the body of the endoscope, wherein the adapter comprises:
- a first connector configured to be attached to and detached from a video processor; and
- a second connector configured to be attached to and detached from the endoscope body, and
- the endoscope circuit board is interposed between the first connector and the second connector.

12. An endoscope power receiving method comprising:
- when an endoscope is connected to an endoscope processor of a first type having only a first power supply,
  - receiving power at a first power receiving section of the endoscope from the first power supply; and
  - electricity connecting from the first power receiving section to a first power supply generation IC, a second power supply generation IC, and a third power supply generation IC of the endoscope;
- when the endoscope is connected to an endoscope processor of a second type having the first power supply and a second power supply,
  - receiving power at the first power receiving section of the endoscope from the first power supply;
  - electricity connecting from the first power receiving section to the first power supply generation IC of the endoscope;
  - supplying power from the second power supply to a second power receiving section of the endoscope; and
  - electricity connecting from the second power receiving section to the second power supply generation IC of the endoscope;
- when the endoscope is connected to an endoscope processor of a third type having the first power supply, the second power supply and a third power supply,
  - receiving power at the first power receiving section of the endoscope from the first power supply;
  - electricity connecting from the first power receiving section to the first power supply generation IC of the endoscope;
  - receiving power at the second power receiving section of the endoscope from the second power supply;
  - electricity connecting from the second power receiving section to the second power supply generation IC of the endoscope;
  - receiving power at a third power receiving section of the endoscope from the second power supply; and
  - electricity connecting from the second power receiving section to the third power supply generation IC of the endoscope;
- receiving a signal from a voltage detection circuit only when the endoscope is connected to the endoscope processor of the first type and making the first power supply generation IC, the second power supply generation IC, and the third power supply generation IC electrically conductive; and
- when the endoscope is connected to the endoscope processor of the second type or the third type, not making the first power supply generation IC electrically connecting to the second power supply generation IC and the third power supply generation IC.

* * * * *